(12) United States Patent
Orofino

(10) Patent No.: US 9,549,960 B1
(45) Date of Patent: *Jan. 24, 2017

(54) TOPICAL TRANSDERMAL METHOD FOR DELIVERING NUTRIENTS THROUGH THE SKIN FOR EXPEDITED WOUND HEALING AND SKIN REJUVINATION

(75) Inventor: Donald P. Orofino, Port Washington, NY (US)

(73) Assignee: Neville Pharmaceutical, Inc., Albany, NY (US)

( * ) Notice: Subject to any disclaimer, the term of this patent is extended or adjusted under 35 U.S.C. 154(b) by 217 days.

This patent is subject to a terminal disclaimer.

(21) Appl. No.: 13/552,920

(22) Filed: Jul. 19, 2012

Related U.S. Application Data

(60) Provisional application No. 61/509,559, filed on Jul. 19, 2011.

(51) Int. Cl.
| | |
|---|---|
| *A61K 36/886* | (2006.01) |
| *A61K 33/34* | (2006.01) |
| *A61K 33/24* | (2006.01) |
| *A61K 31/727* | (2006.01) |
| *A61K 31/664* | (2006.01) |
| *A61K 31/675* | (2006.01) |
| *A61K 31/455* | (2006.01) |
| *A61K 31/355* | (2006.01) |
| *A61K 31/201* | (2006.01) |
| *A61K 45/00* | (2006.01) |
| *A61M 11/00* | (2006.01) |
| *A61K 31/198* | (2006.01) |
| *A61K 31/4172* | (2006.01) |
| *A61K 33/06* | (2006.01) |
| *A61K 45/06* | (2006.01) |
| *A61K 9/00* | (2006.01) |

(52) U.S. Cl.
CPC ......... *A61K 36/886* (2013.01); *A61K 9/0014* (2013.01); *A61K 31/198* (2013.01); *A61K 31/201* (2013.01); *A61K 31/355* (2013.01); *A61K 31/4172* (2013.01); *A61K 31/455* (2013.01); *A61K 31/664* (2013.01); *A61K 31/675* (2013.01); *A61K 31/727* (2013.01); *A61K 33/06* (2013.01); *A61K 33/24* (2013.01); *A61K 33/34* (2013.01); *A61K 45/00* (2013.01); *A61K 45/06* (2013.01); *A61M 11/00* (2013.01)

(58) Field of Classification Search
CPC combination set(s) only.
See application file for complete search history.

(56) References Cited

U.S. PATENT DOCUMENTS

| | | | | |
|---|---|---|---|---|
| 6,342,484 | B1 * | 1/2002 | Kulkarni et al. | 514/44 R |
| 6,469,070 | B1 * | 10/2002 | Vanden Berghe | 514/738 |
| 7,629,384 | B2 * | 12/2009 | Fossel | 514/565 |
| 2006/0039935 | A1 * | 2/2006 | Antosh et al. | 424/401 |
| 2006/0100177 | A1 * | 5/2006 | Nishimura et al. | 514/99 |
| 2007/0009469 | A1 * | 1/2007 | Kleinman et al. | 424/70.14 |
| 2010/0331377 | A1 * | 12/2010 | McCord | 514/355 |

OTHER PUBLICATIONS

B2-Riboflavin, Retrieved from URL:<http://umm.edu/health/medical/altmed/supplement/vitamin-b2-riboflavin>, Retrieved on [Feb. 22, 2016].*

* cited by examiner

*Primary Examiner* — Nannette Holloman
(74) *Attorney, Agent, or Firm* — Thomas A. O'Rourke; Bodner & O'Rourke, LLP

(57) ABSTRACT

This invention relates to liquid application for skin rejuvenation created from specific amino acids, lipids, nucleic acids and vitamins. This collection of molecules delivers precisely the factors necessary to a specific site requiring healing; a direct intervention system to most expeditiously remodel skin with building blocks. This delivery is a transdermal topical delivery.

Healing is via specific molecules that engender a false autocoid reaction rapidly followed by an incremental healing-anti-inflammatory response augmented by very specific (GRAS" ingredients in the invention and also recruited from the body to this needy site. Energy is brought to site by transdermally delivered protons and enhanced by the local vascular flow initiated by transdermal molecules.

This delivery system bypasses digestion and dilution. Key is a lipophilic carrier with nuclear and mitochondrial ligands that rapidly penetrate and permeate all membranes and truncates the inflammatory site quickly manifesting curation. Other delivered molecules expedite healing at every level.

48 Claims, No Drawings

TOPICAL TRANSDERMAL METHOD FOR DELIVERING NUTRIENTS THROUGH THE SKIN FOR EXPEDITED WOUND HEALING AND SKIN REJUVINATION

CROSS-REFERENCE TO A RELATED APPLICATION

This application claims the benefit of U.S. Provisional Patent Application No. 61/509,559, filed Jul. 19, 2011, the full disclosure of which is incorporated by reference.

BACKGROUND OF THE INVENTION

Methylation is key to the epigenetic perfect expression, peak maintenance and re-assembly of all genes (DNA/RNA). On the skin surface or wound site, methylation can be part of the energy cycle to facilitate in the epigenome's perfect retooling; the Methyl Nicotinate molecule (MN) is present to affect this reassembly on the skin surface or wound site. This process occurs without any systemic dilution or metabolic transformation that would occur by the oral or parenteral administration of the administered substance. Methyl Nicotinate molecules are lipophilic in nature and at the cellular level easily traverse through the plasma membrane. The methyl group provides energy directly to the site of application on the order of 3 protons (H+) or 12ATP's for every Methyl Nicotinate molecule. Once in the cytosol, it can readily enter the nucleus, delivering the Nicotinate ligand and energy. This Methyl donor energy interacts with the gene (DNA/RNA) via multiple venues; one is the histone sheath. This exposes more of the gene (DNA/RNA), now expressing its increased function and/or repair, and/or gene silencing, and/or its activation of apoptosis. The genome (DNA/RNA) is thus rebooted by the MN thereby allowing epigenetically more of the phenotypic aspects of the gene (DNA/RNA) to facilitate a renewed, reorganized and enhanced structure within the cell. The repaired gene can now perform with greater efficiency, and the repaired cell containing this gene (DNA) becomes more efficient in its innate cellular functions. There is a special energy balancing synergy to maintain perfect structure and function that requires the delicate pre-programming of the following cellular pathways: CAMP, PGC1A, Ppars, Foxol, PARP1a, peroxisomes and proteasomes. These pathways work in synergy, aiding and contributing to optimize each individual cellular mechanism. The protons/ATP, seamlessly delivered, assist with the process of cellular respiration and maintain the balance of NAD, NADH, FAD and FADH.

Whether the gene is carrying out its normal functions or effecting self-repair, it can now do so expediently due to this delivery of energy that is both transdermally applied and systemically recruited via specific nutrients. Where RNAi or the gene has been silenced, or is malfunctioning, the increased energy can retool this nuclear function. If the malfunction is not fixable, this energy can allow the cell to have PARP (parp1 in this case), induce apoptosis or autophagy via demethylization. When and if the cell rejuvenates, in turn, the energy and the nicotinate ligand for the nuclear super family of transcriptional related genes (NSF-TRG) will induce the nucleus to engender increased production of mitochondria, proteasomic activity, Ppars, PGC1a and Sirtuin activations to continue their ever-vigilant maintenance of the gene (DNA).

Through the use of Methyl Nicotinate, the nicotinate ligand, as a promoter of the nuclear super family of transcriptional related genes (NSFTRG), is attracting cytoplasmic organelles into the cytosol for increased mitochondria activity.

Within the barrier of the skin where the wound begins, the nicotinate molecule functions as a false analog, creating a false injury (an autocoid response) that is quickly recognized by the body and is quelled more rapidly than a true injury, then stimulating an anti-inflammatory-healing process. The delivered beta alanine also defuses the inflammatory response allowing the anti-inflammatory response to occur more quickly.

With the absorption and transfer of the array of accompanying materials for rebuilding cellular tissue (dermis), Methyl Nicotinate causes Phase-1 Cell Cycle (G-1) stimulation. This, coupled with MN activation of lipolysis via adipose tissue releasing free fatty acids (FFA), including arachidonic acid (AA) that recruits both the lox cascades and cox cascades, along with a myriad of other cytokines and chemokines. These enable local inflammation at the cell/wound site. There is also a local transformation of stem cells to mast cells with the increased production of histamine and heparin and their powerful antioxidant and anticoagulation effects at the cell site due to this local false inflammatory reaction.

Arachidonic acid by-products are legend. The body will transform AA to leukotriene (LTA4) that hydrates to LTB4. Then glutathione helps engender LTC4 from B4. Removal of specific amino acids manifests D4 and E4 from C4. The healing cascade is as follows: B4 causes adhesion and chemotaxis and Superoxide dismutase (SOD) manufacture and, in general, invites systemic cells to come to this site to assist in a quick/short false inflammatory response. This is followed by a dedicated anti-inflammatory healing response.

The nutrients delivered to the wound site with Methyl Nicotinate are specific for wound/skin healing. This action truncates and expedites the cellular healing process.

The amino acid L-Histidine is a delivered nutrient, whose safety, pharmaceutical evaluation, bioavailability with physiology, metabolism, medical usage and physiologic impact are well documented in the scientific and biomedical literature. Histidine functions as a safe anti-inflammatory and antioxidant. Histidine on its own permeates the skin (integument) to reach the full dermis, down to the keritinocytes, where it renders several restorative functions. Methyl Nicotinate, described above, further enhances tissue penetration and saturation of Histidine while its redox properties allow metal cations, singlet oxygen and hydroxyl groups to be reduced and/or neutralized, and rendered non-toxic. Free. Histidine (HD) is found in all tissue. As HD is decarboxolated to histamine (HA), beta-alanine can combine with HA in the presence of carcinine synthetase forming carcinine (CA). Alternately, HD may combine with beta-alanine, in the presence of carnosine synthetase, to become carnosine.

Carnosine (CS) is important in protein manufacturing and diminishing glycosylation and carbonylation. By the modes of actions of HA/HD/CS/CA cells may restore their intrinsic resting electrical potential. This energizing effect further creates within the epidermal and subdermal layers of the skin the re-scaffolding needed for new tissue formation and for the building from connective tissues using CS, an integral component, along with glycine and imidizole acetic acid (IAA), which are needed to provide for the collagen and elastin formation.

While in the re-scaffolding process, reactive oxygen species (ROS) and nitric oxide synthase (NOS) need suitable blockade occurring via the HD, HA, CA and CS molecules that prevents the oxidative deterioration and weakening of the newly formed scaffolding. In fact, all the nutrients and molecules being delivered to skin/wound have an increased shelf life because of these antioxidant molecules. Quintessentially, HD opens the aquaporine channels (AQP0). Specifically, aquaporine increases the PH within the cell as a signaling mechanism and turns on the calcium channel-signaling pathway that provides cellular hydration directly through aquaglyceroporin channels, as well as a milieu to enhance cellular respiration and increase energy manufacturing. Induced Carcinine (CA): HA, derived from HD, can be biochemically changed to CA via HA combining with beta alanine and P-5-P in the presence of Carcinine synthase. CA is an analog of CS. Although CA is best produced in the central nervous system (CNS) at a rate of 15-fold greater saturation than found in any other tissue, its mode of action for healing is mainly seen through the cardiovascular system. The Epiphenomenon permits CS and CA to work directly to influence an increased blood flow and cardiac output to heal injured tissues. Deep tissue (muscle and fascia) restoration relates to CS presence that is essential with deep wound healing. CA directly decreases and/or reverses skin aging. The transdermal mechanism allows application and delivery to the exact area of injury of HD, HA, MN, CS, CA, amino acetic acid (AA), IAA, glycine, P-5-P, Copper (CU++), and the medium chain triglycerides (MCT) molecules that the integument requires for repair. These restorative nutrient components are either applied to the site of repair or are biochemically and/or physiologically produced in situ or alternatively delivered to the site by bodily circulation and/or neurologic discharge.

Additional concentrations of HA and HD pool at injury sites acutely by proximal neural firing. This effects increased HD and HA locally. HA and HD may then be oxidized along with beta alanine to amino acetic acid, and/or imidazol acetic acid (IAA), and/or they can be methylated. Pain at the N-Methyl D-Aspartate (NMDA) sites may be mitigated by IAA occupying the glycine receptor adjacent to the glutamate site. HD is ubiquitous and creates special prostaglandins of the 2 series (PGE2) at the inflammatory sites, which assist in creating accelerated tissue growth. HD and HA, with their bio-degratory amino acetic acids (AAA) are integral in nucleic acid production, essential for new cell growth and replenishment.

Energy for healing is essential. Methyl Nicotinate, a nicotinic acid (B3), with a methyl group attached for its lipophilicity, transports and transfers energy locally. Nicotinate increases the surface temperature of the skin (warming) and causes a significant release of prostaglandins (PGE 2) from the skin. It stimulates histamine release from mast cells in the tissue, thereby initiating the autacoid response of the specific immune system. Methyl Nicotinate, a forerunner of NADPH and NADH are the keys in glucose metabolism. They are required for the energy production needed for healing. This action is accomplished through the donation of an electron, resulting in increased energy for rapid and repeatable cellular tissue repair.

Methyl nicotinate synergizes with pyridoxal-5-phosphate (P-5-P) and cu++ to promote scaffolding for the collagen elastin infrastructure and to efficiently reassemble "big" collagen (potential scarring) to normal collagen. The direct infusion of cu++ increases skin growth and matrix molecules for faster keritinocyte growth, thereby yielding faster dermal growth. A nicotinic acid receptor, known as the G-Protein-Coupled Receptor G(1), is highly expressed in adipose tissue. Including both methyl nicotinate and nicotinic acid in this formula promotes a two-pronged "time released" effect on G(1).

Pyridoxal-5-phosphate (P-5-P) assists in energy production, and in wound/skin methylation by direct application to the site of injury. Like Methyl nicotinate it bypasses per oral digestion and systemic dilution, locally empowering this wound/skin site to grow and heal more rapidly than normal. P-5-P directly facilitates copper in the proper redox state to avoid toxicity, thereby increasing the reactive oxygen species (ROS) being neutralized. The increased bioavailability of the vitamin C for tissue factors (e.g. Glycosaminoglycan) is enhanced by healthy copper at the wound site. P-5-P is a critical factor for the supply of energy, materials and preparation required for on site healing.

Ceramide manufacture, engendered by niacin, increases skin production, along with signaling molecules for apoptosis, cell growth and/or cell differentiation.

Medium Chain Triglycerides (MCT's) are structured lipids C-6 through C-12 that are applied topically to the wound to assist in energy, cell wall manufacture and healing.

Heat Shock Proteins (HSP). The induced local inflammatory site engenders heat shock proteins (HSP) to assist in the chaperoning of specific molecules to their necessary destination of skin and soft tissue remanufacturing sites. Additionally, heat shock factors (HSF1) partner in this same process.

Ribosome switches, or Ribo switches, are now recognized as one of the major metabolite controlling systems that account for about two percent (2%) of genetic regulation in bacteria. They respond to various metabolites, including co-enzymes, sugars, nucleotide bases, amino acids and cat-ions. With Thiamine, Methyl donor groups, glycine and B-alanine, the ribo switches can be turned on, off and incrementally speed up the healing of skin/wounds, bypassing part of the molecular networking that could impede this process.

Sirtuins are necessarily activated by the upstream and downstream energy circuitry that is engendered by multiple networking molecules (CREB, CREM, CAMP, FOXO1, FOXO3a, PPARS, and PGC1a). PGC1a becomes a special additional immediate fuel source for SIRTS by its manifold acetylated lysines. This entire energy loop is the source for wound healing. The above is engendered in part or all by the methylation process and redox upregulation by Methyl Nicotinate, P-5-P, Cu and Inosine (a nucleoside). Inosine is a necessary precursor of cellular energy and efficiency. It sustains cellular and extra cellular ATP for integument maintenance and growth. In new skin formation it enables oxygenation and new ATP manufacture essential for growth. Its neuro protectant application is essential for preservation and regrowth of neural tissue in the healing wound. Inosine is commonly found in tRNA that impacts on RNA editing and RNAi for maximal cellular integrity.

Additional transdermal nutrient delivery molecules in this invention that augment efficacy and potency of this invention are (1-5):

1. ALA (alpha lipoic acid) a thiol and antioxidant that interacts with lipid and water soluble antioxidants increases peak longevity of these several nutrients. ALA reboots vitamin C, vitamin E, ubiquinone and glutathione thereby reducing ROS yet increasing local nutrient bioavailability. ALA architecturally undergirds new dermal growth with glycine and imidizole acetic acid (IAA) allowing dermal structure to emerge under the scrutiny of a genetic cleavage system (caspase proteases) under the protection of the above antioxidants. It also increases eNOS (endothelial nitric oxide synthase) and increases nitric oxide vasodilation.

2. Beta-alanine, above biochemically discussed and applied in earlier text here, is key to the remodeling of injured, diseased or aged skin, suppresses leukotriene (LT) especially LT (B4) thereby diminishing the circadia of the false inflammatory autocoid response of methyl nicotinate (MN) and thus more rapidly engenders an anti-inflammatory healing response.

3. Glycerol, propylene glycol and polysorbate 20 allow more efficient transdermal penetration of molecular substrate. These hydroscopic nutrients with medium chain triglycerides (MCT's) enable enhanced dermal permeation and therefore expedited regrowth.

4. Thiamine enables pyruvate dehydrogenace activity to increase by energizing all cellular rejuvenatory capacity via the TCA cycle and thus defusing neuropathy, myopathy, vasculopathy and endocronopathy.

5. Riboflavin, in addition to its manifold attributes, provides the litmus test of transdermal penetration of this invention by the increased yellow intensity of the urine as absorption crescendos and later decrescendos. It visually depicts the transdermal invention as transit through your body.

All of these nutrients, whether supplied transdermally or recruited to the site, play an important role in the accelerated healing and/or rejuvenation that takes place with this unique formulation and delivery system.

Aquaporins ("AQPs") constitute a major conduit for movement of water across plasma membranes. AQP0 is expressed in the fiber cells. AQP0, engendered by Histidine, is critical for cell homeostasis. Several cellular functions have been attributed to AQP0. In vitro and ex vivo experiments have confirmed the water permeability function of AQP0. It is our belief that AQP0 performs cell-to-cell adhesion. There is strong support and empirical data validating the possible structural role of AQP0 as a cell-to-cell adhesion protein influencing subdermal ceramides.

BRIEF SUMMARY OF THE INVENTION

This present invention relates to specific and highly selective proteins, amino acids, and nucleic acid molecules. This compound has sequences encoding such proteins, nutrient catalyzing cofactors, antibodies and short antisense-like molecules existing and innate within the sub dermal layer. Also included are specific functional methods to enable and utilize such polypeptides to modulate healing, apoptosis, riboswitch-like activation and curation of wounds. The active ingredients are all GRAS ("generally regarded as safe") and all natural. They are factors in the apoptotic cascade, and in the control and modulation of said bodily processes specifically present for the purpose of wound curation and truncation of the insult/injury cycle. The inherent synergy between components provides for an internal milieu that utilizes the body's own recovery cycle and the antisense-like technology underscored by this invention. It provides a time-staged delivery of beneficial nutrients transdermally through the medium of a methyl carrier for the purpose of cellular remodeling, as well as cleavage, by a variety of different caspase proteases that are capable of inhibiting apoptosis.

Mitogen-activated protein kinase kinase kinase 1 is an enzyme that in humans is encoded by the MAP3K1 gen. MAP3K, or MEK kinase, is a serine/threonine kinase that occupies a pivotal role in a network of phosphorylating enzymes integrating cellular responses to a number of mitogenic and metabolic stimuli, including insulin and many growth factors. Mouse genetics has revealed that the kinase is important in correct embryogenesis, keratinocyte migration, T cell cytokine production and B cell antibody production.

DETAILED DESCRIPTION OF INVENTION

1. I have discovered that a variety of nutrients (i.e. vitamins, trace minerals, fats and select amino acids) delivered transdermally/topically in a staged and sequential manner, through the conveyance of a methyl carrier, methyl nicotinate, provide a meaning fu l, measureable and significant way to both induce and transport these active healing substances. This combination of amino acids and mineral cofactors enables the body's own healing and innate immune system to recreate a healed dermis now in homeostasis.

2. The components of this mixture include but are not solely limited to alpha and gamma tocopherols, B-complex vitamins: especially nicotinic acid, the amino acids glycine and histidine, histamine, beta-alanine and taurine, copper and magnesium, P-5-P, polysorbate 20, glycerol, medium chain triglycerides, glycerophosphocholine ("gpc"), propylene glycol, oleic acid, MN, Inosine, and water.

Representative Formulation of Ingredients—Percent & Volume

The composition of the present invention preferably has an active ingredient component and an inactive ingredient component. The composition of the present invention is preferably a solution that includes as an active component a methyl nicotinate component in an amount of about 0.1% to about 0.4%. There may be additional active components. These active components can preferably include one or more of the following:

Arachidonic Acid—0 to 3%
Amino Acidic Acid—0-5%
Histidine—0-8%
Copper Peptide—0-5%
Ascorbyl Palmitate—0-3%
Niacinamide/Nicotinic Acid—0-3%
Histamine—0-5%
Beta Alanine—0-4%
Hypoxanthine Riboside—0-2%
Mixed Tocopherals (Vitamin E) 0-2%
PSP—0-5%
Glycine—0-2%
Taurine—0-2%

Conditional Ingredients (Alpha Lipoic Acid, Carnosine, Inosine): 0-2%, or increase to 5% for wound care applications only. The ingredients as volume percent In addition to the active components there is preferably an inactive component to the solution. The inactive component can include one or more of the following:

Inactive Ingredients
Glycerol—0-2%
Caprylic/Caprilate Triglycerides (MCT) 0-3%
Polysorbate 20—0-1% (sufficient to mix oils/H2O to give emulsion): Preferred is a natural source such as coconut
Propylene Glycol—0%-15% max (solvent in cosmetics)
Phosphatidylcholine—0-3%
Lysophosphatidylcholine—0-0.1%
Ethanol (sufficient to pass Micro biological Assay test)
Glyceryl Stearate—0-1% (emulsifier)
Oleic Acid (sufficient to pass thru the dermis only)
Tetrasodium EDTA (stabilizer)
*Deionized Water—Balance of Solution An example of a preferred composition is as follows:
Ingredients as volume percent Active Ingredients 26.5%-27%
Methyl Nicotinate—0.25%-1%
Arachidonic Acid—1%
Amino Acidic Acid—3%
Histidine—5%
Copper Peptide—3%
Ascorbyl Palmitate—1%
Niacinamide/Nicotinic Acid—0.5%-1%
Histamine—3%
Beta Alanine—2%
Hypoxanthine Riboside—1%
Mixed Tocopherals (Vitamin E) 1%
PSP—3%
Glycine—0.5-1%
Taurine—1%
  Conditional Ingredients (Alpha Lipoic Acid, Carnosine, Inosine): 1%, or increase to 3% for wound care only
Inactive Ingredients
*Deionized Water—Balance of Solution
Glycerol—0.5-1%
Caprylic/Caprilate Triglycerides (MCT) 2%
Polysorbate 20-0.5% (sufficient to mix oils/H2O to give emulsion): natural source coconut
Propylene Glycol—0.5%-10% max (solvent in cosmetics)
Phosphatidylcholine—1%
Lysophosphatidylcholine—0.02%
Ethanol (sufficient to pass Micro biological Assay test)
Glyceryl Stearate—0.5% (emulsifier)
Oleic Acid (sufficient to pass thru the dermis only)
Tetrasodium EDTA (stabilizer)
  * Water is the overall solvent for many of the ingredients, but to formulate the spray most effectively water and fat-soluble emulsions must be homogenized for best transdermal bioavailability and application.

3. The components of this mixture are used in a combination in range used to treat medical conditions in human patients. Topical and/or transdermal treatment is preferred for local control of disease states and inflammatory cascade states to insure that any disparate and/or unwanted side effects are minimized and curtailed.

4. Varieties or combinations of this therapy include, though are not limited strictly to the following:
  (a) A topical/transdermal spray using a radiating pump dispenser,
  (b) A topical/transdermal salve/balm rubbed into the skin;
  (c) A topical/transdermal gel w/aloe vera and vitamin E rubbed into the skin;
(d) A topical/transdermal wound/burn cleansing rinse;
(e) A topical/transdermal roll-on for pain relief;
(f) An impregnated mini-sponge individually hermetically sealed with said composition that can be reconstituted with water,
(g) A wound powder composed of micronized, freeze dried material used for pressure ulcers and diabetic wounds, and
(h) A time-released epidermal/topical patch for staged and sequential delivery of said composition for site-specific application.

I claim:

1. A method of supplying a therapeutic agent locally to a tissue wound site of a patient, said method comprising the steps of:

a) applying a blend of a carrier and a treatment agent transdermally to said tissue wound site to heal said wound site; and b) testing urine of said patient having said damaged tissue for an increase of yellow color to verify, or determine the extent of, transdermal penetration of the blend at the tissue wound site;

wherein said carrier comprises methyl nicotinate for delivering energy to said wound site and for facilitating gene repair and beta-alanine for accelerating an anti-inflammatory response;

wherein said blend comprises active ingredients that enable healing by accelerating tissue growth and that stimulate the immune system to heal the damaged tissue;

wherein said active ingredients for wound healing comprise said methyl nicotinate, arachidonic acid, hypoxanthine riboside, histadine, said beta-alanine, glycine, taurine, pyridoxal-5-phosphate, trace minerals including copper, optionally histamine and optionally imidazole acetic acid;

wherein said hypoxanthine riboside acts as a precursor of cellular energy and, together with said methyl nicotinate, said pyridoxal-5-phosphate, and said copper, facilitates methylation and redox up-regulation;

wherein said glycine and said beta-alanine are included in said blend, in part, for activation of ribosome switches to speed up healing of said damaged tissue;

wherein said blend also contains at least one member selected from the group consisting of glycerol, polysorbate 20, and propylene glycol to promote transdermal penetration; and wherein said blend further comprises riboflavin, said riboflavin providing an indicator of the effectiveness of the topical absorption of the blend.

2. The method according to claim 1, wherein the trace minerals also include magnesium, or blends thereof.

3. The method according to claim 1, wherein the blend further comprises an excipient.

4. The method according to claim 3, wherein the excipient is polysorbate 20.

5. The method according to claim 1, wherein said blend further comprises glycerol or at least one derivative thereof.

6. The method according to claim 5, wherein the derivative of said glycerol is a medium chain triglyceride.

7. The method according to claim 6, wherein the triglyceride comprises a caprylic or caprylate triglyceride.

8. The method according to claim 5, wherein the derivative of said glycerol is glycerolphosphocholine ("gpc").

9. The method according to claim 1, wherein the blend further comprises a solvent.

10. The method according to claim 9, wherein said solvent comprises propylene glycol.

11. The method according to claim 1, wherein the blend is applied using a radiating pump dispenser.

12. The method according to claim 1, wherein the blend is applied as a salve or balm rubbed into the skin.

13. The method according to claim 1, wherein the blend is a gel.

14. The method according to claim 13, further comprising aloe vera and vitamin E.

15. The method according to claim 1, wherein said blend is applied as a wound cleansing rinse.

16. The method according to claim 1, wherein said blend is applied as a burn cleansing rinse.

17. The method according to claim 1, wherein said blend is packaged in an individually hermetically sealed package and wherein said blend has been dehydrated, but may be reconstituted with water.

18. The method according to claim 1, wherein said blend is applied as a powder comprised of micronized, freeze dried material.

19. The method according to claim 18, where said blend is used to treat pressure ulcers.

20. The method according to claim 18, where said blend is used to treat diabetic wounds.

21. The method according to claim 1, wherein said blend is applied by a time-released epidermal/topical patch for staged and sequential delivery of said composition for site-specific application.

22. The method according to claim 1, wherein the treatment agent comprises an anticoagulant.

23. The method according to claim 22, wherein said anticoagulant is heparin.

24. The method according to claim 1, wherein the treatment agent causes an autocoid that engenders dermal healing.

25. The method according to claim 1, wherein the treatment agent further comprises an antioxidant.

26. The method according to claim 1, wherein the treatment agent further comprises an anti-inflammatory agent.

27. The method according to claim 1, wherein the treatment agent is applied to keratinocytes and causes accelerated new dermal growth.

28. A method for supplying a therapeutic agent locally to damaged tissue of a patient, said method comprising the step of:
   applying a blend of a carrier and a treatment agent topically to said damaged tissue to heal said damaged tissue;
   wherein said carrier comprises methyl nicotinate for delivering energy to said wound site and for facilitating gene repair and beta-alanine for accelerating an anti-inflammatory response;
   wherein said blend comprises active ingredients that enable healing by accelerating tissue growth and that stimulate the immune system to heal the damaged tissue;
   wherein said active ingredients comprise said methyl nicotinate, arachidonic acid, hypoxanthine riboside, histadine, said beta-alanine, glycine, taurine, pyridoxal-5-phosphate, trace minerals including copper, optionally histamine and optionally imidazole acetic acid;
   wherein said hypoxanthine riboside acts as a precursor of cellular energy and, together with said methyl nicotinate, said pyridoxal-5-phosphate, and said copper, facilitates methylation and redox up-regulation; and
   wherein said glycine and said beta-alanine are included in said blend, in part, for activation of ribosome switches to speed up healing of said damaged tissue.

29. The method according to claim 28, wherein the carrier further comprises copper peptide.

30. The method according to claim 29, wherein the carrier further comprises said pyridoxal-5-phosphate.

31. The method according to claim 30, wherein the carrier further comprises at least one ingredient selected from the group consisting of niacinamide and nicotinic acid.

32. The method according to claim 30, wherein the blend includes riboflavin, and further comprising observing urine of said patient having said damaged tissue to determine effectiveness of absorption of said treatment agent.

33. The method according to claim 28, wherein the trace minerals include magnesium.

34. The method according to claim 1, wherein the treatment agent further comprises fats.

35. The method according to claim 1, wherein the treatment agent further comprises vitamins and said vitamins include ascorbyl palmitate and tocopherols.

36. The method according to claim 1, wherein said blend is applied by a roll on applicator.

37. The method according to claim 1, wherein said blend is applied by a blend impregnated mini-sponge.

38. The method according to claim 1, wherein said blend contains inactive ingredients and from about 0.1 to about 1 vol. % of said methyl nicotinate;
   wherein said inactive ingredients comprise water, ethanol, medium chain triglycerides and glycerol.

39. The method according to claim 1, wherein said blend further comprises up to 1 vol % of said arachidonic acid, up to 2 vol. % of said hypoxanthine riboside, up to 8 vol. % of said histidine, up to 5 vol. % of said glycine, up to 4 vol. % of said beta-alanine, up to 2 vol. % of said taurine, and up to 5 vol. % of said pyridoxal-5-phosphate.

40. The method according to claim 1, wherein said blend contains up to 3 vol. % of said arachidonic acid, and also up to 3 vol. % of nicotinic acid, up to 2 vol. % of beta and gamma tocopherols, up to 3 vol. % of ascorbyl palmitate, up to 3 vol. % of caprylic/caprylate triglycerides, up to 3 vol. % of phosphotidyl-choline, and up to 5 vol. % of copper peptide.

41. The method according to claim 1, wherein said blend also contains one or more additional ingredients selected from the group consisting of alpha-lipoic acid, carnosine, and thiamine, said thiamine providing further assistance for activation of said ribosome switches.

42. The method according to claim 1, wherein said blend further comprises alpha-lipoic acid, carnosine, and said imidazole acetic acid, but in a sum total amount of not greater than 5 vol. %, and wherein said alpha-lipoic acid acts together with said glycine and said imidazole acetic acid to promote growth of dermal structure to facilitate local wound healing.

43. The method according to claim 24, wherein the treatment agent that causes an autocoid that engenders dermal healing is decosahexanoic acid.

44. A method for supplying a therapeutic agent locally to damaged tissue of a patient, said method comprising the steps of:
   a. applying a blend of a carrier and a treatment agent topically to said damaged tissue to heal said damaged tissue; and
   b) testing urine of said patient having said damaged tissue for an increase of yellow color to verify, or determine the extent of, transdermal penetration of the blend in the damaged tissue;
   wherein said carrier comprises methyl nicotinate for delivering energy to said wound site and for facilitating gene repair and beta-alanine for accelerating an anti-inflammatory response;
   wherein said blend comprises active ingredients that enable healing by promoting tissue growth and that stimulate the immune system to heal the damaged tissue;
   wherein said active ingredients for wound healing comprise said methyl nicotinate, arachidonic acid, hypoxanthine riboside, histadine, carnosine, said beta-alanine, glycine, taurine, pyridoxal-5-phosphate, trace minerals including copper, optionally carcinine, optionally histamine and optionally imidazole acetic acid;
   wherein said hypoxanthine riboside acts as a precursor of cellular energy and, together with said methyl nicotinate, said pyridoxal-5-phosphate, facilitates methylation and redox up-regulation;

wherein said glycine and said beta-alanine are included in said blend, in part, for activation of ribosome switches;

wherein said blend delivers copper to the damaged tissue; and wherein said blend also contains glycerol, polysorbate 20, and propylene glycol to promote transdermal penetration and riboflavin, said riboflavin providing an indicator of the effectiveness of the topical absorption of the treatment composition.

45. The method according to claim 44 wherein said copper is delivered to the damaged tissue biochemically.

46. The method according to claim 44 wherein said copper is delivered to the damaged tissue produced in situ.

47. The method according to claim 44 wherein said copper is delivered to the damaged tissue by locally increased circulation.

48. The method according to claim 44 wherein said copper is delivered to the damaged tissue by locally increased local neurologic discharge.

* * * * *